United States Patent [19]

Hudleson et al.

[11] 4,232,680
[45] Nov. 11, 1980

[54] APPARATUS AND METHOD FOR TRANSCUTANEOUS ELECTROTHERAPY NERVE STIMULATOR

[76] Inventors: Bruce D. Hudleson, 2920 Ivy St., Titusville, Fla. 32780; Joachim F. Mahnke, 75 Alhambra Dr., Merritt Island, Fla. 32952

[21] Appl. No.: 906,696

[22] Filed: May 16, 1978

[51] Int. Cl.$^2$ ............................................. A61N 1/36
[52] U.S. Cl. .................................................. 128/422
[58] Field of Search ................ 128/416, 421, 422, 804

[56] References Cited

U.S. PATENT DOCUMENTS

| | | | |
|---|---|---|---|
| 3,810,457 | 5/1974 | Bottcher et al. | 128/421 |
| 3,911,930 | 10/1975 | Hagfors | 128/422 |
| 4,062,365 | 12/1977 | Kameny | 128/422 |

Primary Examiner—William E. Kamm
Attorney, Agent, or Firm—Richard D. Dixon

[57] ABSTRACT

The present disclosure relates to a method and apparatus for being used in transcutaneous electrical nerve stimulation. The apparatus includes a first circuit operatively coupled to a source of electrical energy for generating a squarewave output signal. At least two pads are provided for being placed in operative communication with the skin adjacent to the body sections of the patient to be treated. A second circuit is provided having an input operatively coupled to the first circuit and having outputs operably coupled to the pads. The second circuit amplifies the squarewave signal from the first circuit so as to deliver at the outputs thereof a predetermined constant current squarewave output signal representative of the input signal. In this manner the area of the body operably interposed between the pads will be treated by the squarewave signal having a predetermined constant current level which is independent of the operative resistance of the body section between the pads.

22 Claims, 4 Drawing Figures

APPARATUS AND METHOD FOR TRANSCUTANEOUS ELECTROTHERAPY NERVE STIMULATOR

BACKGROUND OF THE INVENTION

I. Field of the Invention

The present invention is related to an electrotherapy apparatus of the type used for transcutaneous electrical nerve stimulation. In particular, the present invention relates to an electrical device which generates a square-wave output signal having a constant predetermined current which is independent of the resistance of the section of the body to be treated.

II. Description of the Prior Art

The use of electromagnetic radiation for medically treating sick or injured patients is well represented in the prior art. For example, diathermy treatments were originally developed to utilize the heating effect of high frequency electromagnetic energy in order to treat muscular disorders. More recently X-ray and gamma radiation have been utilized in the control of malignant tumors such as cancer.

The recent introduction of acupuncture medical techniques has stimulated medical research as to the operative medical connection between the nervous system and the normal functioning of other body organs. The results of this medical research indicates that the functioning of and pain sensation produced by many of the body organs may be regulated through the appropriate stimulation of various multiple nerve endings spaced generally away from the particular body organ.

Some medical reserachers have endeavored to combine the teachings of electromagnetic medicine with the teachings of acupuncture medicine, thus resulting in the field of auriculotherapy. One early pioneer in the field of auriculotherapy was Dr. Paul Nogier of France who recognized that certain body conditions could be treated through the application of electrical energy to nerve endings in the ear or auricle. At the present time the typical auriculotherapy device includes a bipolar probe which is utilized to compare the impedance of the human cell tissue between a central point on the bipolar probe and a reference point on the human body with a second point on the bipolar probe and the same reference point, typically a hand-held ground reference potential. Auriculotherapy researchers have recognized that nerve endings typically have lower tissue resistance than the surrounding skin. It is therefore important to locate with sufficient accuracy the nerve endings corresponding to the body organ or area to be treated. Typically the resistance between a key acupuncture point and the reference potential may be on the order of 900 kilo-ohms, while the resistance measured between the surface of the skin not adjacent to a key acupuncture point and the reference potential would be on the order or 1,500 kilo-ohms.

After the impedance differential method has been utilized to locate the key points, the same bipolar probe is typically utilized for applying a low frequency pulsating signal across the acupuncture point. The typical auriculotherapy device applies a known voltage across this impedance in order to develop the flow of a small current through the nerve to be treated, typically on the order of 20 to 100 microamperes.

Since the actual impedance of the different acupuncture or key points as measured across the two elements of the bipolar probe could vary by as much as a factor of 10 depending upon the precise nature of and location of the acupuncture point, the actual current which flows through the acupuncture point cannot accurately or easily be determined. Since recent medical research has revealed that the waveform of and the effective integrated average of current are primarily related to the effectiveness of the application of this electrical energy to the acupuncture points, it has become even more important to accurately regulate the flow of electrical current through the acupuncture point.

While medical research regarding the use of electrotherapy and acupuncture are continuing, up to the present time there has been no definitive consensus as to the effectiveness of this mode and technique of treatment. Therefore, while the Federal Food and Drug Administration has not yet approved this modality of electrotherapy, the FDA has nevertheless agreed not to exert jurisdiction over devices which employ output currents of less than 500 microamperes. Recent medical research, however, has indicated that the level of 500 microamperes of current is more than sufficient for treating the typical patient.

Several different theories have been proposed as to the effectiveness of the electrotherapy techniques. The most simplistic of these theories postulates that the electrical signal applied to the nerve ending merely overloads the nerve and thereby jams the brain's sensing of pain. This theory accounts for the effectiveness of stimulating the corresponding peripheral nerve in the ear as well as the effectiveness of stimulating the corresponding nerve communicating with the section of the patient's body. Not only may these techniques be used for controlling pain, but electrotherapy may also be used to recapture lost motor control of the type experienced in diseases such as Multiple Sclerosis. It has been postulated that the sustained improvement which follows the application of the electrical current to the appropriate acupuncture response point is due to a transient chemical phenomenon which in essence depolarizes the nerve endings in order to increase the output of certain chemicals in the nerve cells. This electrical stimulation improves the synaptic transfer in addition to the transfer of motor commands from the neurons to muscle tissues. See for example, KASLOW & LOWENSCHUSS, *Multiple Sclerosis: Rehabilitation Through Acupuncture-Response Point Therapy*, AM. J. ACUPUNCTURE (Vol. 2, 1974).

Holt, in U.S. Pat. No. 3,718,132, discloses the use of an electrical circuit for generating positive and negative pulses whose vectorial sum is equal to zero. The pulses are applied to the patient through a transformer in order to avoid any shock hazard. The voltage input to the primary winding of the transformer is held constant in an attempt to maintain a constant current output from the transformer. The output voltage is not compensated for variations in the actual impedance of the sections of the body into which the electrical energy is coupled.

In contrast to the prior art references which relate to auriculotherapy, the present invention is specifically designed for transcutaneous nerve stimulation which relates to the direct stimulation of nerves and nerve endings which are proximately related to the location of the section of the body exhibiting pain or nerve impairment. Other critical areas of the body which contain sympathetic nerve endings may also be treated with some success. The advantage of using transcutaneous neuroelectric stimulation (TENS) lies in the fact that the patient may apply this treatment himself rather than requiring the assistance of skilled medical technicians as is the case for auriculotherapy. Furthermore, the accuracy of placement of the electrode pads which impart the electrical signal in (TENS) is noncritical compared to the fine tolerances which must be maintained for the application of the electrical signal in auriculotherapy.

TENS uses the same basic concept as auriculotherapy in order to stimulate the nerve endings or synaps. This electrical stimulation produces an electrochemical change at the nerve endings close to the skin. Positive and/or negative charges travel through the sensory nerves to the brain. The presently preferred method uses a periodic waveform having both positive and negative excursions with the net total dc current equal to zero. This waveform effectively neutralizes any electrical imbalance in either the nerve pathways or in the brain.

By utilizing pads having relatively large surface areas, as compared with the smaller bipolar probes used in auriculotherapy, the patient is able to stimulate a larger number of nerve endings, or in the alternative to lessen the accuracy required in locating the nerve endings. By placing the pads on opposite sides of the body sections to be treated, the patient or operator will improve the probability of operatively coupling with a sympathetic nerve ending which is coupled to the muscle or body organ for which treatment is intended.

Thus, the first object of the present invention is to provide an electrotherapy apparatus and apparatus which utilizes paired pads for coupling a squarewave signal of constant current density for stimulating nerve endings adjacent to the area of the body to be treated.

A second object of the present invention is to provide means for regulating the frequency of the squarewave output signal and to regulate the waveform of the output signal so that it generally exhibits a 50 percent duty cycle with no dc component.

A still further object of the present invention is to provide an indicator signal for indicating when the constant current output of the device is equal to the prescribed current setting.

SUMMARY OF THE INVENTION

The present invention relates to an electrotherapy apparatus for electrically treating a section of a patient's body. The electrotherapy apparatus includes first circuit means operably coupled to a source of electrical energy for generating a squarewave output signal. At least two pad means are provided for being placed in operative communication with the skin adjacent the body sections to be treated. Second circuit means are provided having an input operatively coupled to the first circuit means and having an output operably coupled to the pad means. The second circuit means are provided to amplify the squarewave input signals so as to deliver at the outputs thereof a predetermined constant current squarewave output signal representative of the squarewave input signal thereto. In this manner the area of the body operatively interposed between the pad means will be treated by the squarewave signal having a predetermined constant current level which is independent of the operative resistance of the body section between the pad means.

BRIEF DESCRIPTION OF THE DRAWINGS

Other objects, features and advantages of the present invention will be apparent from a study of the written descriptions and the drawings in which.

DETAILED DESCRIPTION OF THE PREFERRED EMBODIMENT

Figure 1:
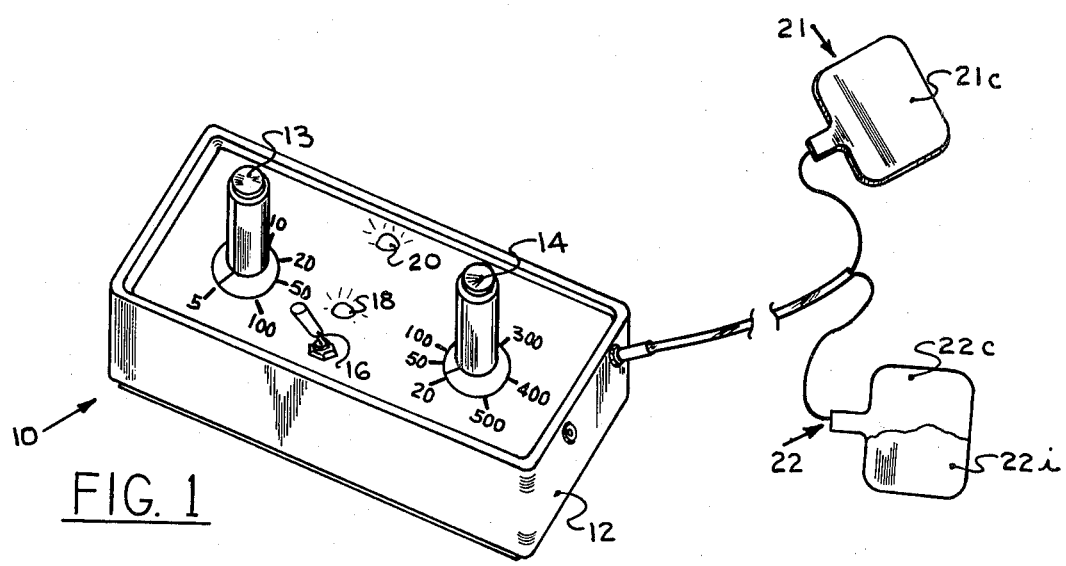
FIG. 1 illustrates a frontal perspective view of a first preferred embodiment of the transcutaneous electrical nerve stimulator in accordance with the teachings of the present invention.

A first preferred embodiment of the transcutaneous electrical nerve stimulator is illustrated generally as 10 in FIG. 1. The apparatus includes a box 12 which is used to contain the battery power supply and the other electronic components constituting the invention. A frequency adjust potentiometer 13 is located on the upper surface of the apparatus for allowing the operator to adjust the frequency of the output squarewave signal. A current adjust potentiometer 14 is located on the upper surface of the unit in order to allow the operator to designate the output current generated from the constant current squarewave generator. An on-off switch 16 applies power to the electrical circuitry and verification thereof is provided by the illumination of the LED 18. Another LED 20 is illuminated for indicating that the unit is supplying the required current as determined by the current adjustment potentiometer 14 into the load represented by the section of the human body coupled between a first pad 21 and a second pad 22.

As illustrated with reference to pad 22, each of the pads is constructed from a generally rectangular sheet of a flexible, electrically conductive substance 22c such as a carbon impregnated silicon compound. This conductive layer 22c is covered by a non-conductive layer 22i which is laminated thereto in order to allow the operator to place the conductive surface 22c into communication with the skin and then to press upon the non-conductive or insulative layer 22i with his hands or with adhesive tape. Typically the pads are of approximately 2 centimeters by 3 centimeters in dimension, but these dimensions may vary depending on the surface area required for proper conductivity.

Figure 2:
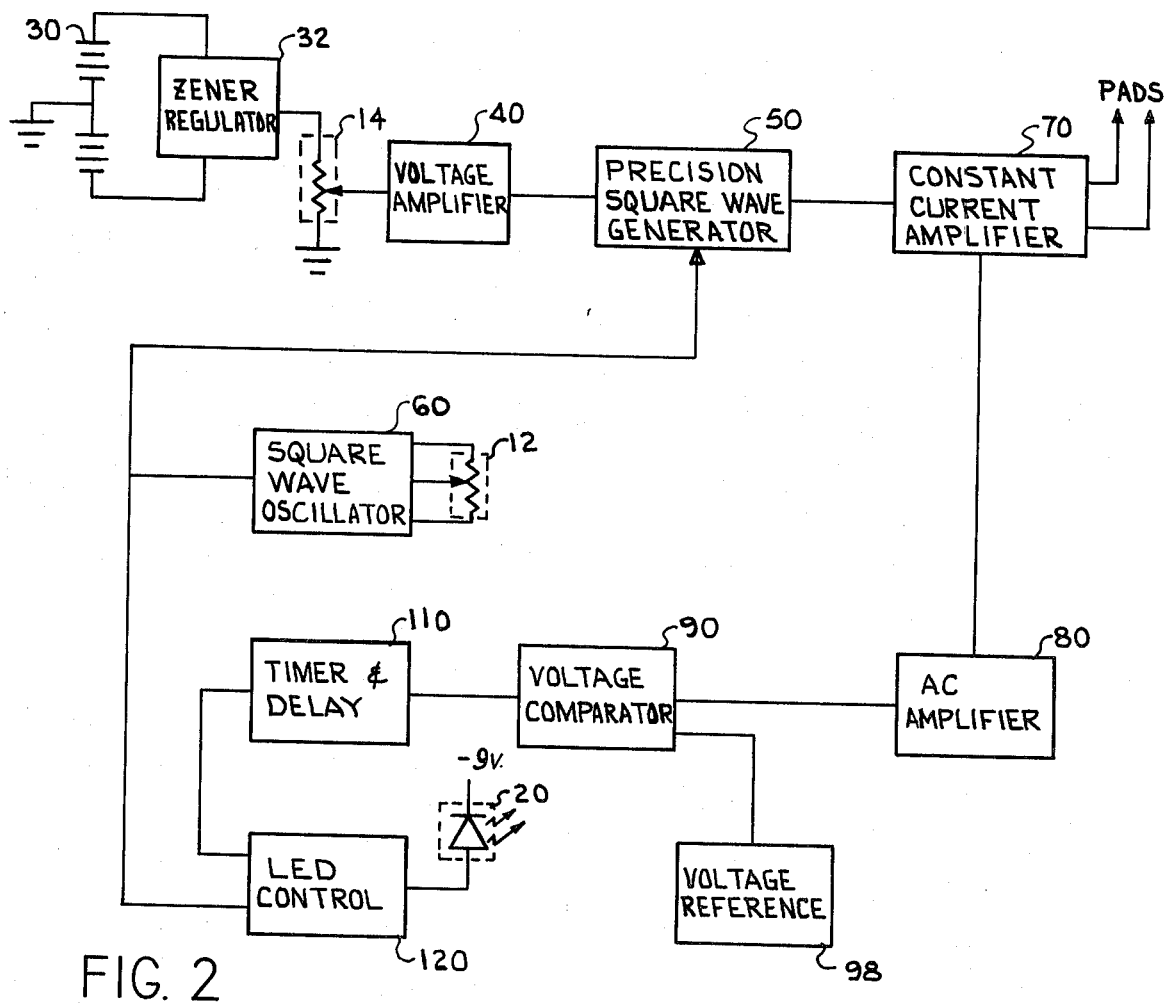
FIG. 2 illustrates a schematic block diagram of the first preferred embodiment of the transcutaneous electrotherapy nerve stimulator.

With reference to FIG. 2, a schematic block diagram for the first preferred embodiment of the transcutaneous electrotherapy nerve stimulator is illustrated as comprising a dc power supply 30 consisting of two groups of two 9 volt batteries each. This power supply 30 is coupled to a Zener regulator 32 for stabilizing a lower output voltage for being coupled to the precision electronics comprising a portion of the present invention. The output of the Zener regulator 32 is coupled through a precision potentiometer 14 which acts as the current adjustment as previously described. This potentiometer 14 actually comprises a voltage divider which feeds a reference voltage to the input of a voltage amplifier 40. The dc voltage output level from the voltage amplifier 40 is fed to the input of a precision squarewave generator 50.

The frequency adjust potentiometer 13 serves as an input to a squarewave oscillator 60 which determines the operating frequency of the transcutaneous electrical nerve stimulator. The operational amplifier 60 is configured with the voltage divider defined by resistor 62 and 63 across the non-inverting input, and with the RC network comprising resistors 12 and 64 in conjunction with the capacitor 61 across the inverting input. As the frequency adjust potentiometer 12 is varied, the period of time required for the output of the operational amplifier 60 to switch between the positive and negative voltage extremes will be varied, thereby adjusting the frequency of the output squarewave signal which is fed through the coupling resistor 65 in order to drive the switching transistor 52. The output of the squarewave oscillator 60 is coupled to the input of the precision squarewave generator 50 for switching the voltage fed from the voltage amplifier 40. The output of the precision squarewave generator 50 comprises a squarewave signal having the frequency determined by the squarewave oscillator 60 and the voltage levels typically centered about 0 volts with a level determined by the output level of the voltage amplifier 40.

This output of the precision squarewave generator 50 is coupled to the input of a constant current amplifier 70 which converts the precision squarewave input voltage to a constant current output squarewave signal which is coupled directly to the pads 21 and 22. Depending upon the setting of the current adjust control 14, the squarewave output signal from the constant current amplifier 70 will vary between 20 and 500 microamperes. The output signal comprises a squarewave typically having a 50 percent duty cycle with essentially no dc component. However, an offset bias may be introduced in order to force the output to include either a positive or negative offset as required. While scientific studies are presently attempting to determine what dc offsets, if any, will enhance TENS treatment, current practice suggests that no dc offset should be utilized.

In order to determine if the constant current amplifier 70 is capable of delivering the required current, an output of the constant current amplifier 70 is coupled to an ac signal amplifier 80 which senses when the constant current amplifier 70 is saturated and therefore unable to deliver the required current. This saturation signal is then coupled through a voltage comparator 90 which compares the level of the saturation signal with a reference voltage from the reference voltage source 98.

With continuing reference to FIG. 2, the voltage comparator 90 compares the saturation signal, which is a squarewave signal of lower amplitude than the output signal, with a dc reference voltage from the source 98. Typically, when the constant current amplifier 70 is in saturation, the saturation signal from the ac amplifier 80 will exceed the dc level from the voltage reference 98, thus indicating that the constant current amplifier 70 is not able to supply the current required through the pads 21 and 22. However, once the constant current amplifier 70 passes into its linear operational region, the saturation signal will no longer exceed the dc reference voltage, thus causing the output of the voltage comparator 90 to actuate a timer and light circuit 110 which in turn will actuate an LED control circuit 120 which will illuminate the current indicator 20. The illumination of the current indicator 20 thus indicates that the constant current amplifier 70 is able to supply, over the full positive and negative voltage swings, the constant current as indicated by the current reference potentiometer 14.

Figure 3:
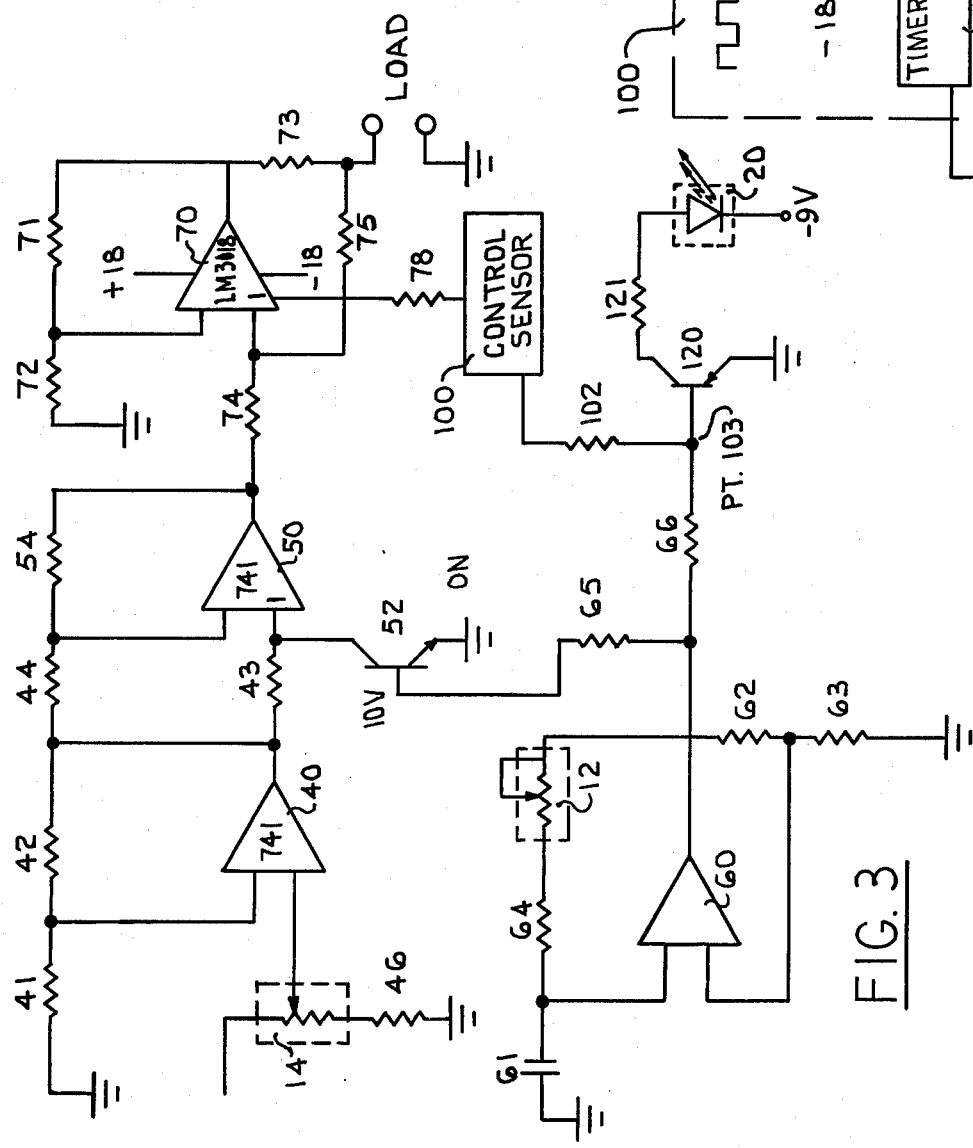
FIG. 3 illustrates a schematic diagram of a first preferred embodiment of the present invention.

With reference to FIG. 3, the regulated output voltage from the Zener regulator 32 is adjusted by the current adjust potentiometer 14 which may be adjusted for up to a +5 volt output. This output is then coupled to one of the inputs of the operational amplifier 40 which serves as the precision dc voltage amplifier. This operational amplifier 40 typically multiplies the dc output voltage by a constant factor of two. The output of the operational amplifier 40 is then coupled to one input of an operational amplifier 50 which serves as the precision squarewave generator.

A switching transistor 52 is also coupled to the input of the operational amplifier 50, and the switching transistor 52 is alternately switched from cutoff to saturation and back to cutoff in response to the output voltage from the operational amplifier 60 which serves as a multivibrator or squarewave generator. When switching transistor 52 is saturated, the first input of the operational amplifier 50 will be shorted to ground and the operational amplifier 50 will operate as an inverting amplifier, thereby giving an output voltage of as much as negative 10 volts. When the switching transistor 52 is cut-off, the operational amplifier 50 becomes a noninverting amplifier having a gain of 1, thereby causing the output to go to as much as positive 10 volts. Therefore, the output of the operational amplifier 50 will alternate between plus and minus a voltage determined by the current adjustment potentiometer 14 at a frequency determined by the frequency adjust potentiometer and the multivibrator 60. As previously stated the actual voltage output level from the operational amplifier 50 is determined by the setting of the current adjust potentiometer 14. In actual operation the squarewave output from the operational amplifier 50 may be varied between 0.8 to 20 volts peak-to-peak.

The constant current amplifier 70 comprises an operational amplifier, typically a LM 3108 which is configured so as to transform the input voltage waveform to a constant current output signal which is then coupled to the load, typically the pads 21 and 22. The current output of the operational amplifier 70 is determined by the values chosen for the feedback resistor 71, the input resistor 72 and the scale resistor 73. The series resistor 74 and the forward sensing feedback resistor 75 also provide additional linearity to the operation of the constant current amplifier 70. Therefore, dependent upon the peak-to-peak voltage level of the squarewave input signal to the constant current amplifier 70, the output of the amplifier will be a squarewave having the peak current independent of the value of the load resistance. That is, the peak current will be determined by the level of the precision voltage at the input of the operational amplifier 70, as long as this amplifier is not in saturation. Typically this constant current amplifier is designed to produce from between 20 and 500 microamperes of current into the typical output load.

With continuing reference to FIG. 3, the output of the constant current amplifier 70 existing at pin 1 of the LM 3018 is coupled through the resistors 78 to the input of a control sensor subsystem shown generally as 100. The output of the control sensor 100 is coupled through a resistor 102 to the circuit point 103. The control sensor 100 operates so as to distinguish the operating point of the constant current amplifier 70. This is, the control sensor 100 will sense if the constant current amplifier 70 is operating in its linear range, thereby being capable of regulating the flow of current therethrough to achieve the constant current function, as opposed to being in the saturated state which indicates that the amplifier is not capable of regulating the current flowing therethrough.

When the control sensor 100 sense that the constant current amplifier 70 is in the linear or nonsaturated state, the control sensor subsystem 100 will generate an enable signal which is then coupled through the resistor 102 to the circuit point 103. When the enable signal from the control sensor 100 is added to the squarewave output from the oscillator 60, the switching transistor 120 will be alternatively switched on and off for allowing current to flow through the LED 20. When the control sensor 100 senses that the constant current amplifier 70 is saturated, this enable signal will not be present and the current indicator 20 will not be illuminated. Thus, the illuminator of the current indicator 20 signifies that the constant current amplifier 70 is conducting its linear operational mode and is therefore capable of regulating the flow of a constant current therethrough.

In a second preferred embodiment of the present invention it is envisioned that the absence of this enable signal may be coupled to the frequency control feedback loop of the squarewave oscillator 60, such as through a varicap, in order to instruct the squarewave oscillator 60 to increase the frequency of the squarewave generated thereby. In this manner the control sensor 100 would automatically control the frequency of the squarewave signal output of the oscillator 60 in order to obtain the lowest possible frequency at which the constant current amplifier 70 was capable of controlling in a linear manner the output current waveform therefrom.

A unique circuit has been devised for sensing when the constant current generator 70 comes out of saturation and begins operating in a linear range, which is of course the desirable mode for a constant current amplifier. As illustrated in resistor 78 is coupled to pin 1 of the operational amplifier 70 (typically the LM 3018) for receiving from this device a signal comprising a dc component of a approximately 15 volts negative polarity and superimposed thereon a squarewave of the same waveform and frequency but of smaller amplitude as the output waveform of the constant current generator 70. When the constant current amplifier 70 is in saturation, the amplitude of the squarewave signal will be approximately 1 volt peak-to-peak, whereas when the operational amplifier 70 comes out of saturation and begins to operate in its linear mode the peak-to-peak amplitude of this squarewave signal will become typically less than 0.1 volts.

Figure 4:
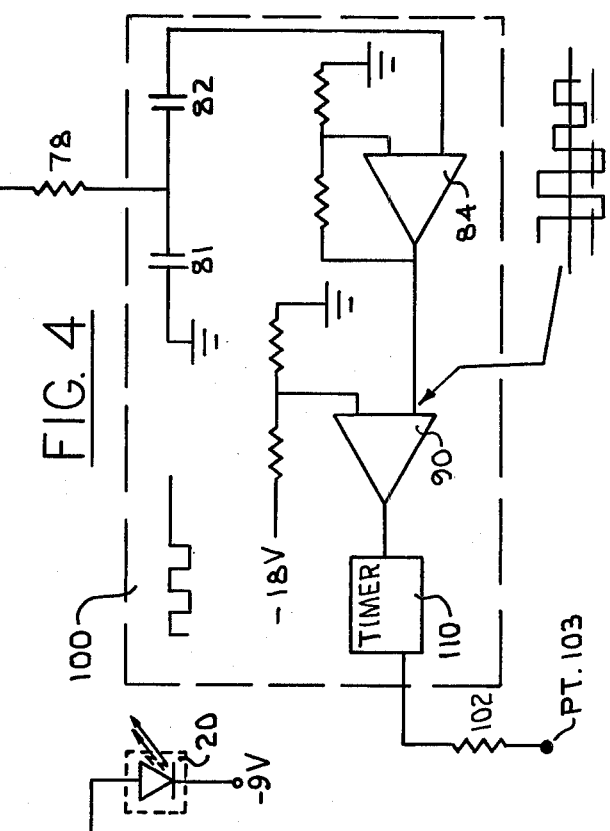
FIG. 4 illustrates a schematic diagram of a first preferred embodiment of the circuit for sensing the saturation of the constant current signal generator.

As illustrated in FIG. 4, this composite output signal is then fed from the resistor 78 through the coupling capacitor 82 in order to remove the minus 15 volt dc component therefrom. This squarewave ac signal is then coupled through an operational amplifier 84 which has a gain of approximately 7.2 for amplifying the output level of this low level squarewave signal. The output signal from operational amplifier 84 is fed to one input of a voltage comparator 80. A second input of the voltage comparator 80 is fed with a precision dc voltage level for being compared with the level of the squarewave input. Typically the dc voltage level is approximately 3.6 volts while the squarewave output of the ac amplifier 84 is approximately plus and minus 5 volts. Therefore, the output of the operational amplifier 80 will follow the squarewave output of the amplifier 84 when the constant current amplifier 70 is in saturation. As the constant current amplifier 70 comes out of saturation and progresses into its linear operating mode, the squarewave output of the amplifier 84 will not exceed the negative 3.6 volts, thereby preventing the output of the voltage comparator 80 from following the squarewave output of the amplifier 84. Thus, when the constant current amplifier 70 operates in the linear region the output of the voltage comparator 80 will remain high.

The output signal from the voltage comparator 80 is coupled to the input of a timer 110. The timer 110 generates an enable signal through resistor 102 only when the output signal from the voltage comparator 90 remains high for at least 0.3 seconds. As previously explained, when the enable signal together with the squarewave output from the oscillator 60 are mixed together, the two signals will actuate the switching transistor 120 for allowing current to flow through the resistor 121 and into the LED indicator 20. This indicates that the constant current amplifier 70 is operating in its linear range and therefore is capable of providing the required constant current output regardless of the exact value of the resistance between the pads 21 and 22.

The operation of the transcutaneous electrotherapy nerve stimulator in accordance with the present invention will now be described with reference to FIGS. 1,2,3, and 4. First, a saline solution, which may consist of table salt mixed with water, or a conductive gel is applied to the area of the body to which the pads are to be attached. Typically one pad is placed on one side of the body appendage so that a center line drawn between the pads passes through the area to be treated. Experience on certain areas of the body indicates that the pads may be moved slightly in order to maximize the effectiveness of this treatment. The conductive surfaces of the pads 21c and 22c are then coupled through the saline solution or the conductive gel to the area of the body to be treated. The pads 21 and 22 may be taped to the area to be treated, or in the alternative the patient may grasp the insulated sides 21i and 22i of the pads 21 and 22 in order to provide pressure to improve the electrical coupling between the pads and the body.

Next, the main power switch 16 is actuated for supplying electrical power to the circuitry. The current adjustment potentiometer 14 is then adjusted to read 500 microamperes while the frequency adjustment potentiometer 13 is adjusted to 100 Hz. If the current indicator LED 20 is illuminated, then the frequency adjustment potentiometer 13 should be rotated counter clockwise to reduce the operative frequency of the squarewave output signal until the current indicator 20 is no longer illuminated. The operator then incrementally increases the frequency using the frequency adjustment potentiometer 12 until the current indicator 20 is again illuminated. If it is not possible to illuminate the current indicator 20 even after the frequency adjustment potentiometer 13 is rotated completely counterclockwise, then with the frequency adjustment potentiometer 13 set on 5 Hz the current adjustment potentiometer 14 should be rotated counterclockwise in order to reduce the current which must be maintained through the pads 21 and 22. After a period of current application to the area of the body, the body tissue becomes more conductive and the current adjustment potentiometer 14 may be slowly increased.

In order to obtain the most effective relief from pain, the output current should be maximized and the frequency should be minimized. However, the current indicator 20 should always remain illuminated thereby indicating to the patient that precisely the correct output current is being provided between the pads 21 and 22. The duration of the treatment is generally dependent upon the type of physical problem which is being treated, but typically an application of 5 to 6 minutes is sufficient to achieve reasonable relief from pain caused by the following conditions: arthritis, lower back pain, bursitis, post operative pain, frozen shoulder, tennis elbow, common bruises, muscle spasms and migraine headaches. In the case of migraine headaches it is suggested that in order to avoid the annoyance of flashes which appear in front of the eyes when excessive current is applied to the temple areas of the head the current adjustment potentiometer 14 should be set in the range of 150 to 200 microamperes at a frequency of 100 Hz for a period of 15 minutes. The frequency of treatments using this device and method will be dependent upon the type of condition to be treated and the extent to which pain has already progressed. For example, in some cases it is necessary to apply these treatments three times per day, while in other cases one treatment per month is sufficient. One primary advantage of the present invention is that the patient himself may determine when additional treatments are required and may administer these treatments to himself. This should be contrasted with auriculotherapy which requires the patient to be treated by a medically trained technician, with this treatment typically not being available at the home of the patient.

Thus, a first preferred embodiment and an alternate embodiment of the transcutaneous electrotherapy nerve stimulator have been described as examples of the invention as claimed. However, the present invention should not be limited in its application to the details and constructions illustrated in the accompanying drawings or the specification, since this invention may be practiced or constructed in a variety of other different embodiments. Also, it should be understood that the terminology and descriptions employed herein are used solely for the purpose of describing the general construction and the operation of the preferred embodiment, and therefore should not be construed as limitations on the operability or possible improvements of the present invention.

We claim:

1. An electrotherapy apparatus for electrically treating a section of the patient's body, said electrotherapy apparatus comprising in combination:
   first circuit means operatively coupled to a source of electrical energy for generating a squarewave output signal;
   at least two pad means for being placed in operative electrical communication with the skin adjacent the body section to be treated; and second circuit means having an input operatively coupled to said first circuit means and having an output operatively coupled to said pad means, said second circuit means for amplifying said squarewave signal so as to deliver at said output thereof a constant current squarewave output signal representative of said squarewave signal at the input thereof, with said second circuit means further including current regulator means for holding constant the current level of said constant current squarewave output signal independent of the operative resistance of the body section between said pad means, whereby the area of the body operatively interposed between said pad means will be treated by said constant current squarewave output signal having a predetermined constant current level.

2. The electrotherapy apparatus as described in claim 1 further comprising frequency variable means operatively coupled to said first circuit means for controlling the frequency of said squarewave output signal and said constant current squarewave output signal.

3. The electrotherapy apparatus as described in claim 2 wherein the frequency range of said constant current squarewave output signal is continuously variable over the range of at least 5 Hz to 100 Hz.

4. The electrotherapy apparatus as described in claim 2 wherein said constant current squarewave output signal includes a dc component substantially equal to zero.

5. The electrotherapy apparatus as described in claim 4 wherein the duty cycle of said constant current squarewave output signal is approximately 50 percent.

6. The electrotherapy apparatus as described in claim 5 wherein:
   said second circuit means includes current limiting means for limiting the effective current of said constant squarewave output signal responsive to a first signal; and further including
   current level means for generating said first signal representative of the desired effective current of said constant current squarewave output signal.

7. The electrotherapy apparatus as described in claim 6 wherein the effective current of said constant current squarewave output signal is limited by said current limiting means to less than 500 microamperes.

8. The electrotherapy apparatus as described in claim 6 wherein the peak-to-peak voltage of said constant current squarewave output signal is less than 50 volts.

9. The electrotherapy apparatus as described in claim 6 further comprising:
   third circuit means operatively coupled to said second circuit means for generating a current level signal representative of the effective current of said constant current output signal; and
   fourth circuit means operatively coupled to said third circuit means and to said current level means for generating a discernable status signal responsive to said first signal being generally equal to said current level signal, thereby indicating that the effective current of said constant current output signal is generally equal to a desired effective current.

10. The electrotherapy apparatus as described in claim 2 wherein each of said pad means includes an electrical insulative surface and a coplanar electrically conductive surface operably coupled to said outputs of said second circuit means.

11. The electrotherapy apparatus as described in claim 10 wherein said electrically conductive surface is at least 4 square centimeters in area and is sufficiently flexible in order to conform to the shape of the adjacent body surface.

12. A transcutaneous neuroelectric stimulation apparatus for electrically treating a section of the patient's body, said apparatus comprising in combination:
   current generator means for generating at output terminals thereof an output signal having a bipolar waveform, with said current generator means including current regulator means for holding constant the current level of said output signal independent of a change in the output load impedance appearing across said output terminals; and a pair of conductive pads electrically coupled to said output terminals of said current generator means for being placed in operative communication with the patient's skin adjacent the body section to be treated, whereby the area of the body interposed between said conductive pads will be treated by said constant current output signal.

13. The transcutaneous neuroelectric stimulation apparatus as described in claim 12 wherein said current generator means comprises in combination:
a frequency generator for generating a drive signal representative of said output signal; and
amplifier means, having an input coupled to said frequency generator, for generating said output signal at said output terminals thereof.

14. The transcutaneous neuroelectric stimulation apparatus as described in claim 13 wherein said current regulator means further comprises comparator means having a first input coupled to said current generator means for sensing a voltage equivalent of said output signal, said comparator means having a second input coupled to said frequency generator means for sensing said drive signal, with said comparator means generating a visual warning signal responsive to the signal at said first input being non-proportional to the signal at said second input thereof, whereby said visual warning signal will appear responsive to said current generator means operating in a non-linear mode.

15. The transcutaneous neuroelectric stimulation apparatus as described in claim 12 or 14 wherein said output signal comprises a generally symmetrical waveform having a 50 percent duty cycle and having substantially no DC components.

16. The transcutaneous neuroelectric stimulation apparatus as described in claim 12 or 14 wherein said output signal comprises a squarewave signal.

17. The transcutaneous neuroelectric stimulation apparatus as described in claim 12 or 14 wherein said current generator further includes frequency variable means for controlling the frequency of said output signal.

18. The transcutaneous neuroelectric stimulation apparatus as described in claim 12 or 14 wherein said output signal is continuously variable in frequency between 5 Hz and 100 Hz, and has a constant current range between 1 and 500 microamperes.

19. The transcutaneous neuroelectric stimulation apparatus as described in claim 12 or claim 14 wherein said output signal has a maximum peak to peak voltage of greater than 25 volts but less than 47 volts.

20. A transcutaneous neuroelectric stimulation apparatus for electrically treating a section of the patient's body, said apparatus comprising in combination:
frequency generator means for generating a periodic drive signal continuously variable in frequency;
amplifier means having output terminals and having an input coupled to said frequency generator means, said amplifier means for generating an output signal at said output terminals, with said output signal being generally symmetrical, bipolar and without a d.c. component, with said amplifier means further including current regulator means for holding constant the current level of said output signal independent of the output load impedance appearing across said output terminals;
comparator means having a first input coupled to said amplifier means for sensing a voltage equivalent of said output signal, said comparator means having a second input coupled to said frequency generator means for sensing said drive signal, with said comparator means generating a discernible warning signal responsive to the signal at said first input being non-proportional to the signal appearing at said second input thereof; and
a pair of conductive pads electrically coupled to said output terminals of said amplifier means for being placed in operative communication with the patient's skin adjacent the body section to be treated, whereby the area of the body interposed between said conductive pads will be treated by said constant current output signal.

21. A method of treating pain and nervous system disorders in the patient's body, including the steps of:
(a) generating an output signal current of less than 500 microamperes having a periodic and bipolar waveform with substantially no d.c. components;
(b) applying said output signal current to a pair of pads coupled to a section of the patient's body adjacent the pain or nervous system disorders; and
(c) regulating said output signal current to a constant flow of current which is substantially independent of load impedance of the body section between said pads.

22. The method as described in claim 21 wherein step (c) includes a substep of monitoring the current regulation process and generating a warning signal responsive to said output signal current being dependent upon the load impedance.

* * * * *